US011157832B2

(12) United States Patent
Kundu et al.

(10) Patent No.: US 11,157,832 B2
(45) Date of Patent: Oct. 26, 2021

(54) MACHINE LEARNING SYSTEM FOR PREDICTING OPTIMAL INTERRUPTIONS BASED ON BIOMETRIC DATA COLLECTED USING WEARABLE DEVICES

(71) Applicant: International Business Machines Corporation, Armonk, NY (US)

(72) Inventors: Amitava Kundu, Bangalore (IN); Sujan Sarathi Ghosh, Bangalore (IN); Abhijit Singh, Bangalore (IN)

(73) Assignee: International Business Machines Corporation, Armonk, NY (US)

( * ) Notice: Subject to any disclaimer, the term of this patent is extended or adjusted under 35 U.S.C. 154(b) by 871 days.

(21) Appl. No.: 15/846,570

(22) Filed: Dec. 19, 2017

(65) Prior Publication Data
US 2019/0188604 A1 Jun. 20, 2019

(51) Int. Cl.
| | |
|---|---|
| G06F 21/00 | (2013.01) |
| G06N 20/00 | (2019.01) |
| G06F 21/32 | (2013.01) |
| G06F 16/335 | (2019.01) |
| A61B 5/00 | (2006.01) |
| A61B 5/11 | (2006.01) |
| G06F 1/16 | (2006.01) |

(52) U.S. Cl.
CPC ............ *G06N 20/00* (2019.01); *A61B 5/1118* (2013.01); *A61B 5/7267* (2013.01); *G06F 16/337* (2019.01); *G06F 21/32* (2013.01); *A61B 5/7264* (2013.01); *G06F 1/163* (2013.01)

(58) Field of Classification Search
None
See application file for complete search history.

(56) References Cited

U.S. PATENT DOCUMENTS

| | | | |
|---|---|---|---|
| 7,478,129 B1 * | 1/2009 | Chemtob | H04L 12/1827 709/204 |
| 9,501,613 B1 | 11/2016 | Hanson et al. | |
| 2003/0065561 A1 | 4/2003 | Brown et al. | |
| 2005/0015744 A1 * | 1/2005 | Bushey | G06F 8/38 717/104 |
| 2005/0065571 A1 | 3/2005 | Imran | |
| 2007/0265598 A1 | 11/2007 | Karasik | |
| 2012/0011530 A1 * | 1/2012 | Bentolila | G06Q 30/0251 725/14 |
| 2016/0183687 A1 * | 6/2016 | Hoyt | A47C 7/56 297/217.2 |
| 2017/0149580 A1 | 5/2017 | Bazar et al. | |

* cited by examiner

*Primary Examiner* — Andrew J Steinle
(74) *Attorney, Agent, or Firm* — Patterson + Sheridan, LLP

(57) ABSTRACT

Method and apparatus for using machine learning to monitor biometric data to provide intelligent alerts are provided. At a first moment in time, first biometric data for a plurality of users are received from a plurality of sensor devices. A group metric is generated by processing the first biometric data using at least one trained machine learning model, and it is determined that the group metric does not satisfy one or more predefined criteria. At a second moment in time, second biometric data for the plurality of users is received from the plurality of sensor devices, and an updated group metric is generated by processing the second biometric data using the at least one trained machine learning model. Upon determining that the updated group metric satisfies the one or more predefined criteria, an indication is provided that the one or more predefined criteria have been satisfied.

20 Claims, 6 Drawing Sheets

MACHINE LEARNING SYSTEM FOR PREDICTING OPTIMAL INTERRUPTIONS BASED ON BIOMETRIC DATA COLLECTED USING WEARABLE DEVICES

BACKGROUND

The present disclosure relates to machine learning, and more specifically, to using machine learning with wearable technology to monitor biometrics.

The Internet of Things (IoT) is a vast network of devices that can communicate and exchange data, often retrieved from sensors on the device. The IoT includes appliances, vehicles, light switches, watches, televisions, thermostats, security systems, clocks, speakers, as well as many other devices in addition to the more traditional laptops, desktops, and smart phones. In recent years, the IoT has expanded dramatically, and now also includes a wide variety of wearable, implantable, or ingestible devices that can collect biometric data from an individual user. Increasingly, these wearable devices are being employed to monitor medical conditions or symptoms of the user.

For example, this biometric data can be used to determine unsafe health conditions, such as low blood sugar in a user with diabetes. IoT devices can also be employed in beds, chairs, shoes, and anything a user may interact with in a variety of other health-related settings, such as aiding with weight loss, treating weight disorders, stimulating the gastrointestinal tract of the user, monitoring eating habits, observing sleep patterns, and tracking physical exercise activities of the user. In each implementation, however, the wearable device collects health data from a single individual, and there is no system that monitors biometric data across a group of users in order to allow for the aggregation of health data for a variety of purposes relevant to the group, as opposed to merely for the individual user.

SUMMARY

According to one embodiment of the present disclosure, a method is provided. The method generally includes receiving, at a first moment in time, first biometric data for a plurality of users from a plurality of sensor devices. A group metric is generated by processing the first biometric data using at least one trained machine learning model. It is determined that the group metric does not satisfy one or more predefined criteria. Next, at a second moment in time, second biometric data for the plurality of users is received from the plurality of sensor devices, and an updated group metric is generated by processing the second biometric data using the at least one trained machine learning model. Upon determining that the updated group metric satisfies the one or more predefined criteria, an indication that the one or more predefined criteria have been satisfied is provided.

Other embodiments of the present disclosure include a system including a processor and a computer memory storing a program which, when executed on the processor, preforms the methods disclosed herein. An additional embodiment includes a computer-readable storage medium having computer-readable program code embodied therewith, the computer-readable program code executable by one or more computer processors to perform the methods disclosed herein.

DETAILED DESCRIPTION

Figure 1:
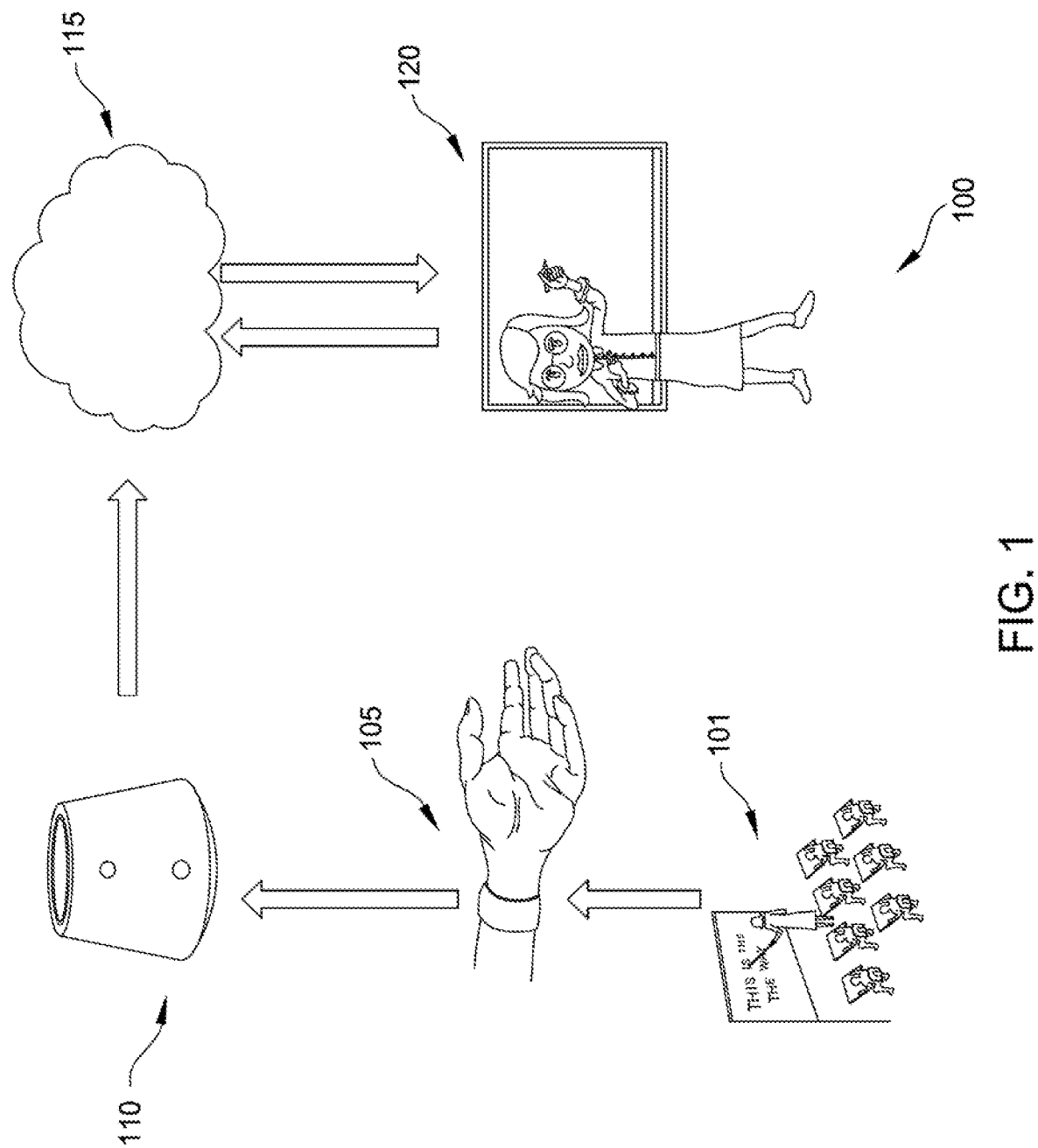
FIG. 1 illustrates an environment for monitoring biometric data of users, according to one embodiment disclosed herein.

Embodiments of the present disclosure enable the collection and aggregation of biometric data for a group of individuals in order to track various medical and health-related conditions and generate health metrics. Groups of people routinely gather for things like meetings, training, seminars, classes, and the like. Typically, there are one or more people who control the pacing and scheduling of the meeting, such as a lecturer, organizer, or speaker. In the process of scheduling an event, it may be important to plan for breaks or pauses during the meeting, particularly if it is a long session. Frequently, these breaks are scheduled ahead of time by the organizers of the event, and include things like coffee or tea breaks, snack breaks, lunch breaks, dinner breaks, and the like. As these are scheduled hours, days, or weeks in advance, they usually occur at particular times, regardless of whether a break is actually required. Further, because these breaks are usually scheduled before the event even begins, they can only be adjusted by a few minutes at most if a speaker continues past the end of his or her allotted time, or a large number of questions are asked of the speaker.

Because these scheduled meetings are fairly rigid in terms of timing and length, the breaks themselves during the event are also relatively immovable. Problematically, this rigidity means that although some attendees may be thirsty, hungry, or ready for a break at the scheduled time, others will not be. The attendees who are not yet ready for a break may have a less productive experience, because they will not want to stop at the scheduled time. Similarly, they will be less attentive later, after the break, if they were not able to use the break to the fullest extent. Further, if the interruption is scheduled too late, some attendees will be hungry, thirsty, or otherwise ready for a break before the break is scheduled, which reduces their productivity as well. For example, these attendees will be less attentive before the break, because they are thirsty, hungry, tired, or otherwise ready for a break, and are not paying attention as much as they could be.

In some meetings or events, it is possible for an individual attendee to leave the meeting in order to take a break. In some instances, however, attendees generally may not come and go without the permission of the speaker. For example, in classroom setting, students may not be allowed to leave the room without permission, and are unlikely to be allowed to take their lunch break at any time other than the scheduled time. Additionally, it is not desirable to leave in the middle of a meeting, as the attendee will miss important information and therefore be less productive. In some smaller meetings, the attendees may work together to decide when to take a break, e.g., by talking with each other and with the speaker. However, this can be a lengthy process that wastes valuable time. Additionally, some or all of the attendees may not want to admit that they want a break. Further, as the group of attendees gets larger, this collaborative decision-making becomes impossible.

In various group activities, this leads to inefficient meetings and reduced productivity, as the break time is rarely at the optimal moment. Embodiments of the present disclosure involve using machine learning to monitor biometric data from attendees at such an event. The biometric data is processed using one or more machine learning models in order to determine whether a break should be initiated. In one embodiment, the data is collected at least in part using wearable devices, such as bands worn on the user's wrist, sensors that are applied to the user's skin, eyeglasses, and any other sensor that can be worn or applied to a user. In some embodiments, the data is collected in whole or in part by implantable devices, such as a device that is surgically implanted, or an ingestible device which the user can swallow. Advantageously, monitoring biometric data using machine learning provides an objective determination that increases efficiency and productivity, and minimizes disruption.

With reference now to FIG. 1, an environment 100 for monitoring biometric data of users, according to one embodiment, is illustrated. The illustrated environment includes a Group of People 101 attending or participating in any group activity. Although a classroom setting is illustrated, the meeting could be a training session, a seminar, a business meeting, and any other group activity where individuals gather. As illustrated, one or more of the users is equipped with a Sensor Device 105, such as a wristband containing one or more sensors for monitoring biometric data of the user. For example, such biometric data can include the heart-rate of the user, blood pressure, body temperature, and components of the user's sweat, tears, saliva, blood, stomach fluids, and the like. In some embodiments, the devices monitor the user's levels of glucose, sugar, lactate, sodium, potassium, proteins, heavy metals, chloride, ammonium, alcohols, peptides, and the like.

In the illustrated embodiment, the biometric data from Sensor Devices 105 is sent from the Sensor Device 105 to a Hub 110. Each Sensor Device 105 may communicate with Hub 110 using any communications method, including wired and wireless communication. In some embodiments, each Sensor Device 105 communicates with Hub 110 using a wireless local area network (WLAN) available in the meeting room, such as a Wi-Fi network. In other embodiments, each Sensor Device 105 communicates with Hub 110 using a personal area network (PAN) such as Bluetooth, or a similar short-range wireless communications technique. Such an embodiment is advantageous for meetings that occur in areas without a WLAN available. For example, many conference rooms or seminar spaces do not provide a local wireless network for attendees, or provide one with a slow connection. Additionally, some meeting spaces may charge users a fee to connect to the wireless network. Thus, in an embodiment, the Sensor Devices 105 communicate directly with Hub 110 using a PAN.

In the illustrated embodiment, Hub 110 communicates with a Cloud Server 115 over a wide area network (WAN), e.g., the Internet. In some embodiments, however, each Sensor Device 105 may communicate with Cloud Server 115 without passing data through Hub 110. For example, if a WLAN connected to the WAN is available, each Sensor Device 105 may communicate with Cloud Server 115 through this local network, and thereby avoid the need for a Hub 110. Similarly, in some embodiments, each Sensor Device 105 is configured to communicate over a WAN directly, without the need for a WLAN or the Hub 110. In other embodiments, Cloud Server 115 is actually present locally, as opposed to operating on a remote server. In such an embodiment, Sensor Devices 105 may communicate with Cloud Server 115 using a PAN such as Bluetooth, a WLAN such as a Wi-Fi network, or any other data communications technique. Thus, although Cloud Server 115 is illustrated as operating in a cloud environment on a remote server, some embodiments include Cloud Server 115 as a local server, or as a component on a local machine.

As illustrated, Cloud Server 115 processes the biometric data recovered by each Sensor Device 105 using one or more machine learning algorithms, as is discussed in more detail below with reference to FIG. 2. Using the biometric data, Cloud Server 115 generates one or more scores quantifying biological metrics of the users. For example, in an embodiment, Cloud Server 115 determines a hunger level of the individual attendees or of the group as a whole, based on the received biometric data, and alerts the Speaker 120 when the level satisfies predefined criteria. For example, in one embodiment, the criteria are met when the determined level exceeds a predefined threshold. In some embodiments, Cloud Server 115 uses machine learning to generate several metrics based on the biometric data. In such an embodiment, the predefined criteria may be that each generated metrics exceed a respective threshold, or that one or more of the metrics exceed a threshold while one or more other metrics are below a threshold. In an embodiment, the criteria are satisfied if any one metric exceeds a predefined threshold, even if the other generated metrics do not. In this way, the system can determine an optimal break time based on biometric data collected in real-time from the users.

In some embodiments, the biometric data is collected and processed continuously and in real time. In other embodiments, however, the data may be collected and processed at discrete intervals, for example, every thirty seconds, every minute, or every five minutes. In an embodiment, this period of time is user-configurable. In another embodiment, the interval may be adjusted dynamically using machine learning techniques, as will be discussed in more detail below. Collecting and processing the biometric data at discrete intervals rather than continuously may be desirable in some embodiments because it may reduce the energy and computing resources required, as well as the amount of network traffic, without excessively sacrificing accuracy.

In an embodiment, Speaker 120 has a device that allows him to interact with Cloud Server 115 about the status of the group. For example, if the attendees are hungry and wish to take a break before the predefined criteria are met, Speaker 120 may indicate to Cloud Server 115 that they are taking their meal break. In response, Cloud Server 115 may update and refine its machine learning model so that it will be more accurate for future use. Additionally or alternatively, in an embodiment, Cloud Server 115 may adjust the predefined criteria, such as adjusting the required threshold. Similarly, once the criteria nave been met and Cloud Server 115 has provided an indication or notification to Speaker 120 that the criteria have been satisfied, e.g., that a threshold has been exceeded, Speaker 120 may inform Cloud Server 115 that the attendees are not hungry, or would rather continue to work. In such an embodiment, Cloud Server 115 may update its machine learning model based on the indication, in order to provide more accurate predictions in the future. In a related embodiment, Cloud Server 115 may adjust the criteria or threshold in addition or in the alternative.

In an embodiment utilizing discrete time intervals for processing the data rather than continuously processing the data as a stream, Cloud Server 115 may further use indications received from the Speaker 120 to adjust the interval at which data is processed. For example, in an embodiment, when Cloud Server 115 receives an indication that the users are beginning a break, Cloud Server 115 determines how much time has elapsed since the last time biometric data from the users was processed to generate the metric. Additionally, Cloud Server 115 may immediately process data from the attendees at the time that they begin their break. If the updated metric meets the predefined criteria, Cloud Server 115 may determine that the interval was too long, and increased sampling would have more accurately predicted the hunger of the users. In such an embodiment, Cloud Server 115 may then shorten the period between samples, so as to process the biometric data with more granularity.

Figure 2:
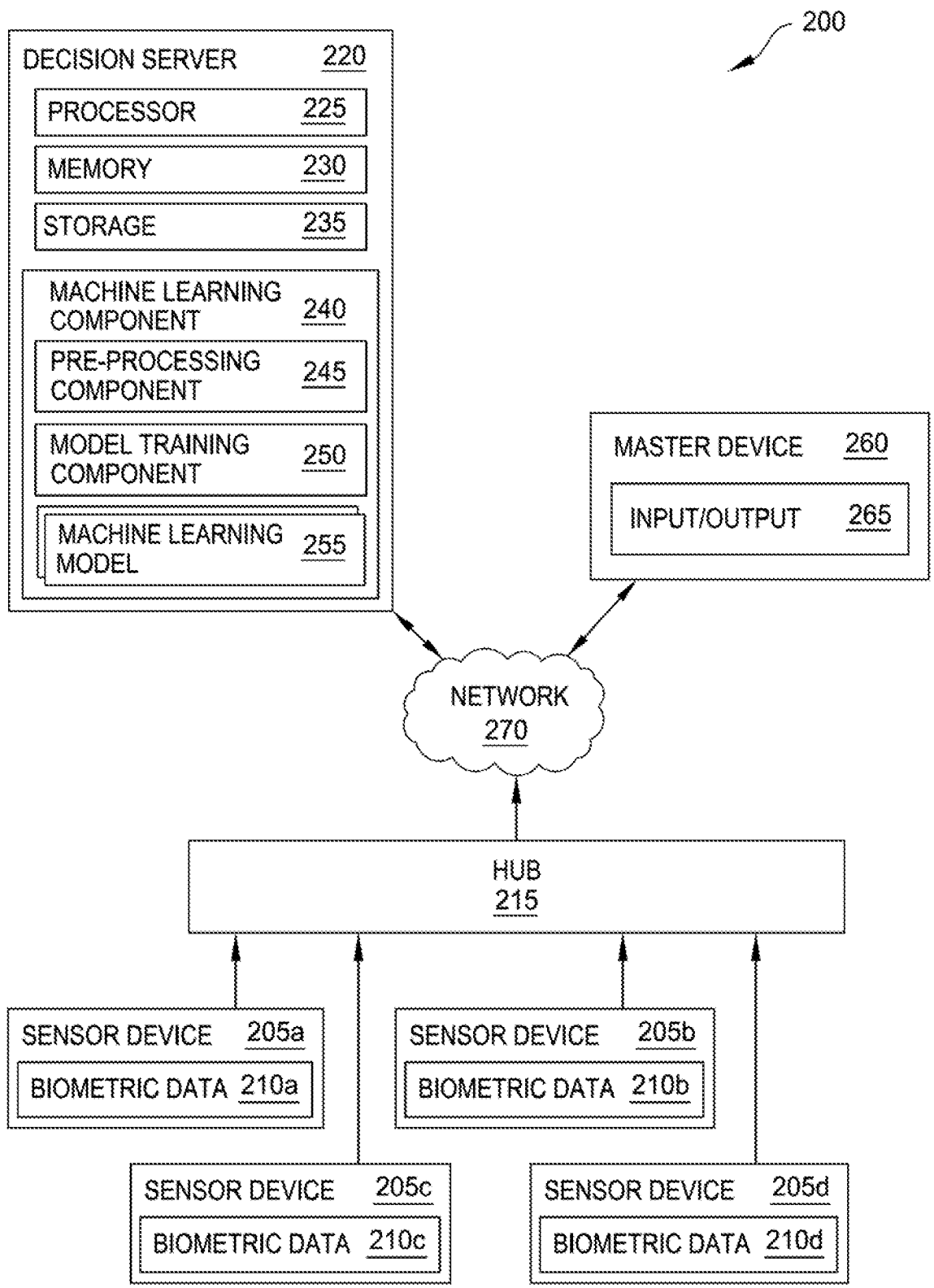
FIG. 2 illustrates a block diagram of a system for monitoring biometric data of users, according to one embodiment disclosed herein.

FIG. 2 illustrates a block diagram of a system 200 for monitoring biometric data of users, according to one embodiment disclosed herein. The illustrated embodiment includes a plurality of Sensor Devices 205a, 205b, 205c, and 205d, a Hub 215, a Master Device 260, and a Decision Server 220. In the illustrated embodiment, Hub 215, Master Device 260, and Decision Server 220 communicate using Network 270, e.g., the Internet. Additionally, each Sensor Device 205a, 205b, 205c, and 205d communicate by using Hub 215, as discussed above. In some embodiments, Master Device 260 communicates through Hub 215 as well, rather than directly through Network 270. Additionally, as discussed above, in some embodiments, Sensor Devices 205a, 205b, 205c, and 205d communicate directly using Network 270, and do not need to involve Hub 215.

As illustrated, each Sensor Device 205a, 205b, 205c, and 205d contain Biometric Data 210a, 210b, 210c, and 210d. That is, each Sensor Device 205a, 205b, 205c, and 205d may collect such Biometric Data 210a, 210b, 210c, and 210d from an individual that uses the Sensor Device 205a, 205b, 205c, and 205d. For example, in an embodiment, each Sensor Device 205a, 205b, 205c, and 205d is a wearable device, such as a wristband, that analyzes the sweat of a user to determine its constituent parts. In this way, Biometric Data 210a, 210b, 210c, and 210d including the levels of glucose, sugar, lactate, sodium, potassium, proteins, heavy metals, chloride, ammonium, alcohols, peptides, and the like can be determined about for each user. Additionally, in some embodiments, Sensor Devices 205a, 205b, 205c, and 205d collect other biometric data, such as the heart rate and body temperature of the user.

As illustrated, Decision Server 220 includes a Processor 225, Memory 230, Machine Learning Component 240, and Storage 235. Processor 225 retrieves and executes programming instructions stored in Memory 230 as well as stores and retrieves application data residing in storage. Processor 225 is representative of a single CPU, multiple CPUs, a single CPU having multiple processing cores, and the like. Memory 230 is generally included to be representative of a random access memory. Storage 235 may be a disk drive storage device, and may include fixed and/or removable storage devices, such as fixed disk drives, removable memory cards, or optical storage, network attached storage (NAS), or storage area-network (SAN).

Machine Learning Component 240 generally processes the biometric data from the users, and generates biological metrics based on that data. As illustrated, Machine Learning Component 240 includes Pre-Processing Component 245, Model Training Component 250, and one or more Machine Learning Models 255. Generally, Pre-Processing Component 245 processes the biometric data in order to facilitate its use with Model Training Component 250 and one or more Machine Learning Models 255, as will be discussed in more detail below. Generally, Model Training Component 250 is used to train and update the one or more Machine Learning Models 255, as will be discussed in more detail below. The one or more Machine Learning Models 255 are used to process biometric data from users and providers and generate biological metrics, as will be discussed in more detail below. Although the one or more Machine Learning Models 255 are illustrated as a part of Machine Learning Component 240, the one or more Machine Learning Models 255 may be embodied in Memory 230, Storage 235, a combination thereof, or any other location capable of performing embodiments of the present disclosure.

In some embodiments, biometric data is provided directly to Model Training Component 250 and Machine learning Models 255 without pre-processing. In other embodiments, however, it is necessary or helpful to pre-process input data in order to facilitate the process. For example, in an embodiment, Pre-Processing Component 245 may generate feature vectors for the biometric data. In this embodiment, a feature vector is a vector having any number of dimensions which represents a numerical representation of the associated data. In some embodiments, this vectorization of the data may improve the speed, efficiency, and/or accuracy of the system. In another embodiment, Pre-Processing Component 245 may process the Biometric Data 210a, 210b, 210c, and 210d to remove outliers, to smooth and/or filter the data, and any other pre-processing that facilitates its use with Model Training Component 250 and Machine Learning Model 255.

Model Training Component 250 generally takes as input biometric data, which may or may not be pre-processed by Pre-Processing Component 245, along with an indication of how hungry the person who provided the biometric data is and generates one or more Machine Learning Models 255 which can be used to classify new biometric data and generate biological metrics. In an embodiment, the indication of the biological metric of the user is a numerical value, for example on a range from 0 to 100, or from 0 to 10, or any other range. In some embodiments, the metric is represented by a rating scale such as a Likert scale with any number of categories (typically five seven, or nine). For example, the metric could indicate how hungry a user is, ranging from "not at all hungry" to "extremely hungry," with any number of options in between.

In the illustrated embodiment, Model Training Component 250 is provided with a set of biometric data and a corresponding set of biological metrics. Thus, when generating or updating a Machine Learning Model 255 for use with user data, an administrator may provide the Model Training Component 250 with biometric data obtained from a user, as well as information about how hungry that user is, as indicated by the user. While processing the training data, Model Training Component 250 creates and updates the respective Machine Learning Model 255. After being trained, the Machine Learning Model 255 can receive as input biometric data and determine how hungry the associated user is. In some embodiments, rather than being trained by an administrator, Machine Learning Models 255 are initiated with arbitrary data, and trained while in use by users. For example, one or more users may wear a Sensor Device 205a, 205b, 205c, and 205d or otherwise provide Biometric Data 210a, 210b, 210c, and 210d to Decision Server 220 throughout their day. At various points during the day, the user may also provide an indication of how hungry they feel. Additionally or alternatively, the user may simply provide an indication of when they ate a meal or snack, or Machine Learning Component 240 may detect that the user is eating or has recently eaten. Using this data, Model Training Component 250 can generate or refine Machine Learning Models 255 to more accurately predict the user's biological metrics.

In some embodiments, there are multiple distinct Machine Learning Models 255 for various users, or various types of users. For example, there may be one Machine Learning Model 255 for each user in a meeting. In such an embodiment, the individual users can train and refine their respective Machine Learning Model 255 as discussed above, e.g., by providing Biometric Data 210a, 210b, 210c, and 210d and an indication of their hunger level throughout the day. Advantageously, this allows for a more accurate model because each user's biometric data is being processed using a model that was trained with that specific user's data. Because an individual's biometric data is likely to vary somewhat from other users, providing a machine learning model unique to each user may improve the accuracy of the system.

In some embodiments, it may not be practical to have a Machine Learning Model 255 unique to each user. For example, in some seminars and meetings, there may be attendees who have never used the system before, or who do not wish to provide such data ahead of time. In an embodiment, there are a number of Machine Learning Models 255, one for each type of user. For example, users may be subdivided into age groups, with one Machine Learning Model 255 for each age group. Of course, any other category of users could also have its own Machine Learning Model 255. For example, the users may be divided into categories based on height, weight, ethnicity, and the like.

As illustrated, each Sensor Device 205a, 205b, 205c, and 205d transmits the Biometric Data 210a, 210b, 210c, and 210d that it collects through Hub 215, which sends the data to Decision Server 220 via Network 270. In an embodiment, Master Device 260 is a component that is used by the speaker, lecturer, or person in charge of the meeting. For example, in some embodiments, Master Device 260 may be a laptop or tablet which the speaker is using during the meeting. In other embodiments, Master Device 260 may be a separate device that is only used for receiving information about the biological metrics from Decision Server 220 and for sending information about the group's activities to Decision Server 220. In some embodiments, Master Device 260 includes a sensor, much like Sensor Device 205a, 205b, 205c, and 205d, such that biometric data is collected and processed for the speaker as well as for each of the attendees. In other embodiments, one of the Sensor Devices 205a, 205b, 205c, and 205d is associated with the speaker, and is a separate device from Master Device 260. Of course, although there are four illustrated, there may be any number of Sensor Devices 205a, 205b, 205c, and 205d. Similarly, though a single Master Device 260 is illustrated, embodiments may have any number of Master Devices 260.

In one aspect, Master Device 260 is configured to receive, from Decision Server 220, information about the determined biological metrics of the users. This information can be provided to the user through Input/Output 265, which may include displays, speakers, vibration components, and the like for output, as well as keyboards, buttons, a mouse, a touch screen, and the like for input. For example, upon receiving an indication from Decision Server 220 that the criteria have been met or exceeded, Master Device 260 may indicate to the user that the criteria have been satisfied. This notification may take the form of vibrations, buzzes, sounds, lights, and/or an indication on a display.

In some embodiments, Master Device 260 may be configured to provide additional information. For example, in some embodiments, Master Device 260 may indicate the current health metrics of the group, as well as the criteria that will trigger a break, such that the speaker can determine how soon a break may be required. For example, if the lecturer has reached a good point to stop and take a break, he or she may check Master Device 260 to see how hungry the attendees are. If the group metric is close to a threshold, the speaker may decide to announce and begin a break, even though the threshold has not been met, because he or she does not want it to interrupt the next part of the meeting.

Additionally, in an embodiment, Master Device 260 is configured to receive input from the user and provide indications to Decision Server 220 about the activity of the group. For example, such an indication may include a notification that the group has stopped working in order to take a break, or that the group is still working despite the fact that the predefined criteria have been satisfied. This information may be provided by the user through a button, touch screen, voice command, or any other technique. For example, upon receiving an indication that a threshold has been reached, the speaker may indicate to the Decision Server 220 that the group is taking a break. In an embodiment, this information can be used to further train and reinforce the Machine Learning Model 255. Alternatively, the speaker may indicate that the group is not yet taking a break. This may be because, for example, the attendees have agreed that they are not yet hungry, or because the speaker wants to finish the topic at hand, so that a new topic can begin after the break. In an embodiment, when an indication is received by Decision Server 220 that the group is continuing to work despite the criteria being satisfied, Decision Server 220 may use this information to further train and refine Machine Learning Model 255.

In an embodiment, each user associated with a Sensor Device 205a, 205b, 205c, and 205d may also provide similar indications to Decision Server 220. For example, if, during a meeting, a user is hungry and wants to take a break, the user may notify Decision Server 220, which may use such indication to refine the Machine Learning Model 255 associated with that user. Similarly, when a break is initiated, a user may indicate that they are not hungry, and thereby cause Decision Server 220 to refine the Machine Learning Model 255 based on this indication.

In an embodiment, Master Device 260 and Sensor Devices 205a, 205b, 205c, and 250d may provide an indication that Decision Server 220 should not use the feedback from the users in training the one or more Machine Learning Models 255. For example, if a group decides to continue working to finish a topic, but the group is in fact hungry, they may indicate to Decision Server 220 that, although they are continuing to work, the prediction was accurate and the Machine Learning Models 255 should not be refined based on the fact that they are not taking a recess. As another example, if the group takes a break for some other reason, such as because of a fire drill, one or more users, including the speaker, may provide an indication that they are not stopping because of hunger, and that the Machine Learning Models 255 should therefore not be adjusted based on the unexpected break.

In some embodiments, in addition to or instead of relying on users to provide indications of whether or not a break is being initiated, Decision Server 220 can be configured to automatically determine whether the users are still engaged in the group activity or not. For example, in one embodiment, each of the Sensor Devices 205a, 205b, 205c, and 205d may be equipped with a location sensor, such as a global positioning system (GPS), or some other location system. Upon detecting that one or more of the users have left the meeting location, Decision Server 220 may determine that they are no longer participating in the group activity, e.g., that a break has been initiated, and may further refine the Machine Learning Models 255 based on this data. Additionally, in some embodiments, Decision Server 220 may monitor the users for indications that they are eating or have eaten recently. For example, a change in glucose or sodium levels may indicate food consumption. Generally, any method of detecting food consumption may be employed, including sensor devices to track muscle movement (e.g., chewing or stomach muscles), audio devices, and the like.

In another embodiment, each user may have a computing device that they interact with during the group activity. For example, each user may be provided with a device to answer questions during the meeting, e.g., to allow the user to vote in a survey or poll. Similarly, each user may be using a laptop, tablet, or mobile device to participate in the activity, or to take notes about the activity. In such an embodiment, Decision Server 220 is configured to detect that one or more users have stopped interaction with their computing devices, and thereby determine that a break has been initiated. For example, if a predefined time period has passed without one or more users interacting with their devices, Decision Server 220 may determine that a break has begun. Similarly, Decision Server 220 may determine that the speaker has not interacted with a respective device for a predefined period of time, and thereby determine that the group activity has been paused. For example, such a device could include a laptop, tablet, or mobile device used to run a presentation. Regardless of whether Decision Server 220 is informed of the status of the group or determines the status autonomously, Model Training Component 250 can use this information to further refine the Machine Learning Models 255, in order to provide more accurate predictions for future use.

In an embodiment, refining the Machine Learning Models 255 is achieved in much the same way as the initial training. For example, upon determining that the generated prediction was wrong, e.g., the users have continued to work even though the most recent generated group metric satisfied the predefined criteria, Model Training Component 250 may be used to refine the Machine Learning Models 255. This refinement generally comprises using Model Training Component 250 to process the current biometric data from the users, along with the determination or indication regarding the group activity. Using this data, Model Training Component 250 can further train and refine the respective Machine Learning Model 255.

In some embodiments, rather than being used by a group of users engaged in a group activity such as a meeting, lecture, seminar, or class, the system can be used by a single individual. For example, as discussed above, an individual may train a Machine Learning Model 255 using their own data, and thereby enable more accurate predictions for themselves. In an embodiment, in addition to training the model, the user may also apply the system to their daily routine. For example, Decision Server 220 may be used to continuously monitor biometric data from the user, process it using the user's own Machine Learning Model 255, and provide an indication to the user that his health metrics satisfy predefined criteria. Such an embodiment may be useful, for example, for individuals who find themselves deeply engaged in their projects, such that they may forget to take breaks, e.g., to eat. Advantageously, the system may provide reminders to the individual based on the user's actual objective biometric data, rather than a simple timer or based on more subjective criteria.

Similarly, an embodiment with a single user can be a useful tool for health monitoring and weight loss. For example, a user may be required to monitor their own biometrics for a variety of reasons, such as diabetes or other illnesses. In a related embodiment, a user may eat even when they are not hungry, or because they cannot tell whether they are hungry or not. In such an embodiment, the system can be deployed to provide information to the user about whether they are objectively biologically hungry, as opposed to merely psychologically hungry, for example, because it is around lunch time. This can enable individuals to better understand their metabolisms and to achieve and maintain a healthy weight, as the system provides objective criteria and determinations.

Figure 3:
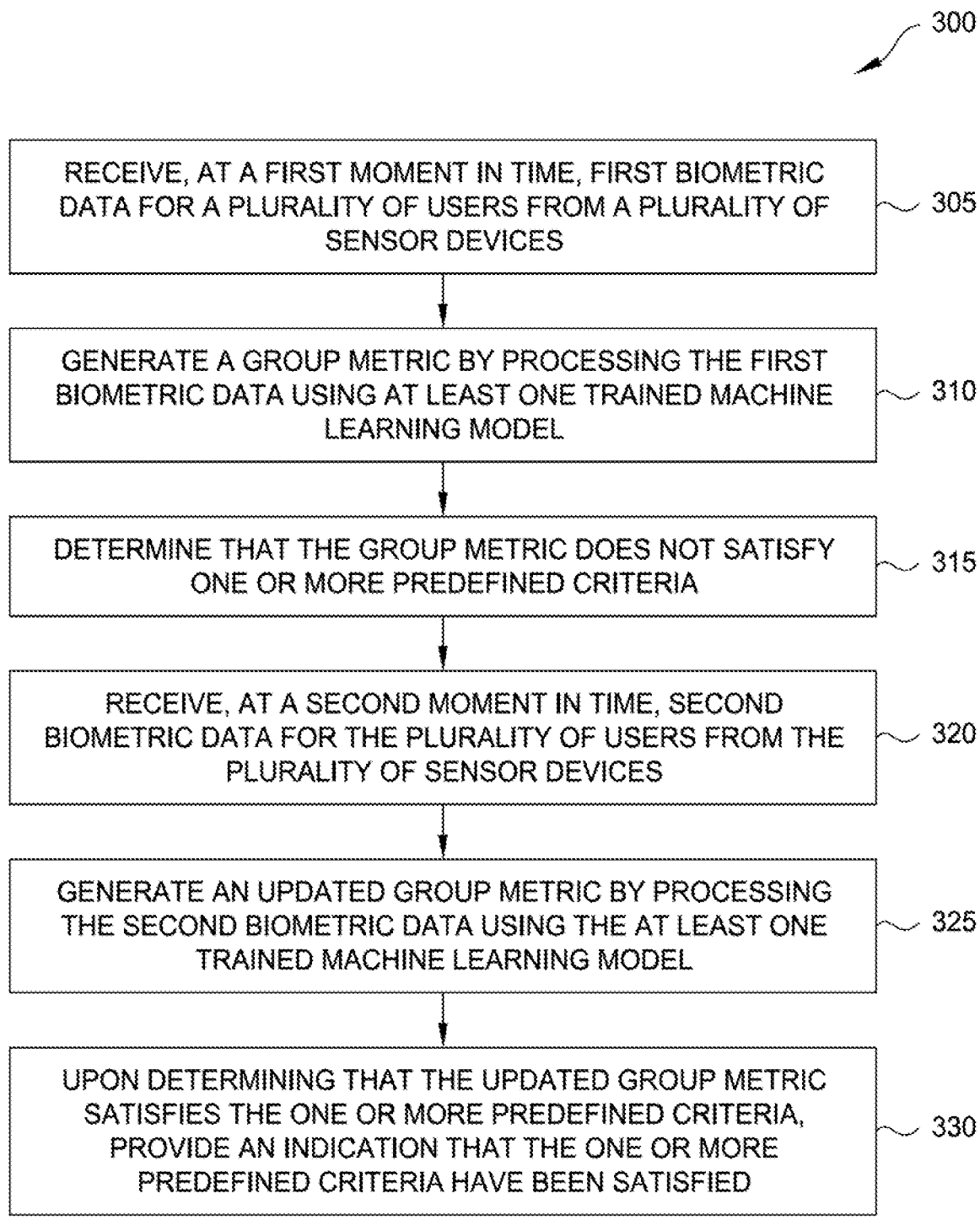
FIG. 3 is a flow diagram illustrating a method for using machine learning to monitor biometric data, according to one embodiment disclosed herein.

FIG. 3 is a flow diagram illustrating a method 300 for using machine learning to monitor biometric data, according to one embodiment disclosed herein. The method 300 begins at block 305, where Decision Server 220 receives, at a first moment in time, first biometric data for a plurality of users from a plurality of sensor devices. At block 310, Machine Learning Component 240 generates a group metric by processing the first biometric data using at least one trained machine learning model. For example, the group metric could indicate an aggregate level of hunger for the group. In some embodiments, in order to generate the group metric, the biometric data from each user is aggregated prior to being processed by Machine Learning Model 255. For example, the data may be summed and averaged, so as to anonymize the data. This average biometric data for the group can then be processed, to generate a group metric for the attendees. In such an embodiment, the biological metric, e.g., hunger level, of any individual attendee is not known, even by the system. This helps to maintain the privacy of the user.

In some embodiments, the biometric data for each user is processed separately, and the resulting individual metrics are combined into the group metric. This is necessary if, for example, one or more users have their data processed with a personalized Machine Learning Model 255. In such an embodiment, once individual metrics have been generated, they may be aggregated, such as by averaging them, to determine the group metric. Of course, in some embodiments, some data may be aggregated before being processed, and some may be aggregated after. For example, in an embodiment providing different Machine Learning Models 255 for different types of user, the data within each group may be combined prior to processing via the respective Machine Learning Model 255, and subsequently the metrics for each category may be aggregated to form the group metric. For example, the biometric data for those aged 35 and older may be aggregated and processed using one Machine Learning Model 255, while the biometric data for those younger than 35 is aggregated and processed by a second Machine Learning Model 255. The generated metrics from each Machine Learning Model 255 can then be aggregated to form a single group metric, e.g., a unified aggregate hunger level for all of the attendees.

At block 315, it is determined that the group metric does not satisfy one or more predefined criteria. Next, at a second moment in time, second biometric data for the plurality of users is received from the plurality of sensor devices at block 320. At block 325, Machine Learning Component 240 generates an updated group metric by processing the second biometric data using the at least one trained machine learning model. Finally, at block 330, upon determining that the updated group metric satisfies the one or more predefined criteria, an indication that the one or more predefined criteria have been satisfied is provided.

Figure 4:
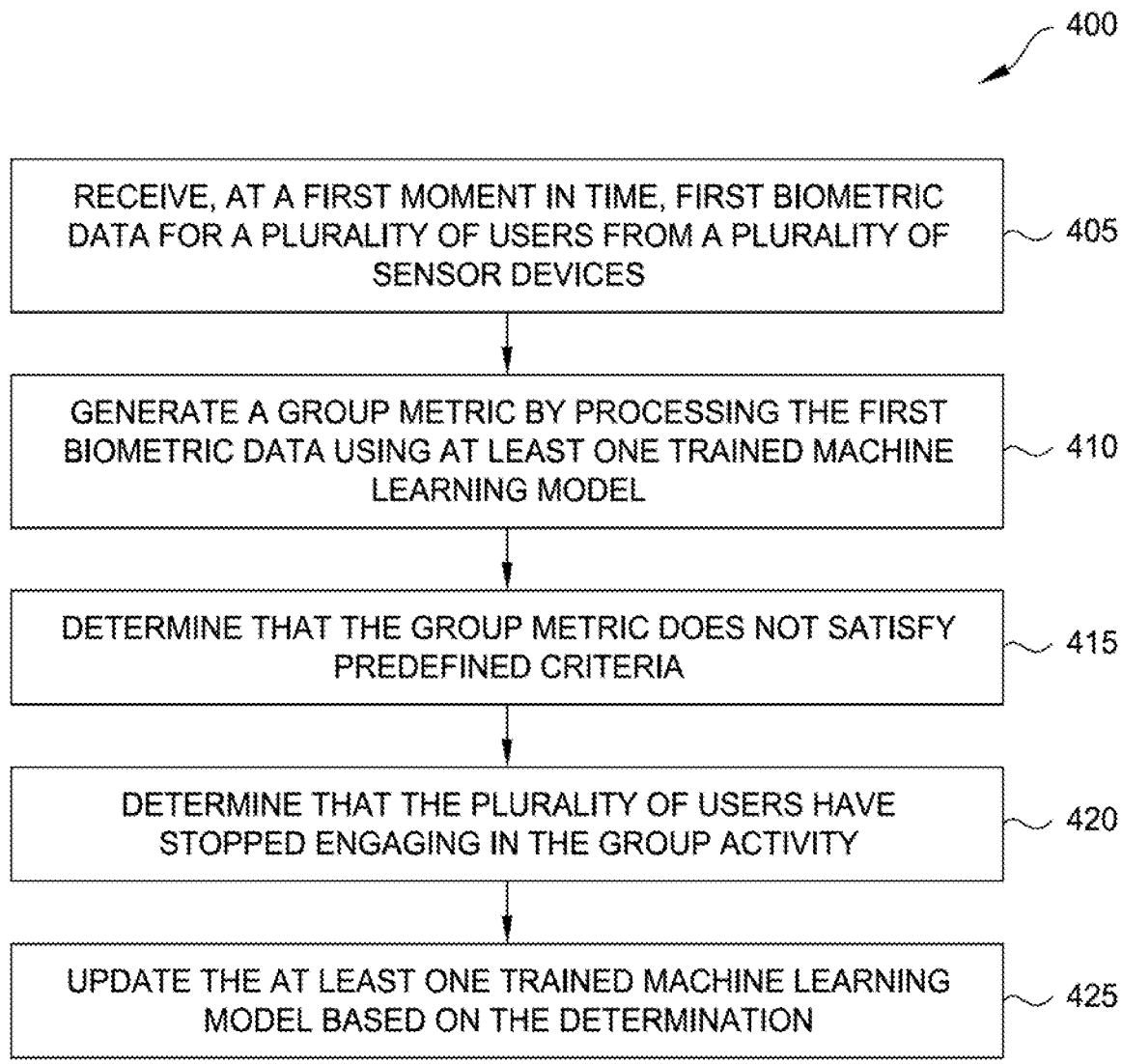
FIG. 4 is a flow diagram illustrating a method for using machine learning to monitor biometric data, according to one embodiment disclosed herein.

FIG. 4 is a flow diagram illustrating a method 400 for using machine learning to monitor biometric data, according to one embodiment disclosed herein. The method 400 begins at block 405, where at a first moment in time, first biometric data for a plurality of users is received from a plurality of sensor devices. Next, at block 410, Machine Learning Component 240 generates a group metric by processing the first biometric data using at least one trained machine learning model, and at block 415, it is determined that the group metric does not satisfy predefined criteria. At block 420, Decision Server 220 determines that the plurality of users have stopped engaging in the group activity. Such a determination could be, for example, based on receiving an indication from one or more users that they are taking a break. As discussed above, the determination could also be based on the detected location of one or more of the users, based on the interaction of the users with computing devices, based on detecting that the users have eaten, or any other methodology. Finally, at block 425, the at least one trained machine learning model is updated based on the determination. This refinement may be performed by, for example, Model Training Component 250.

Figure 5:
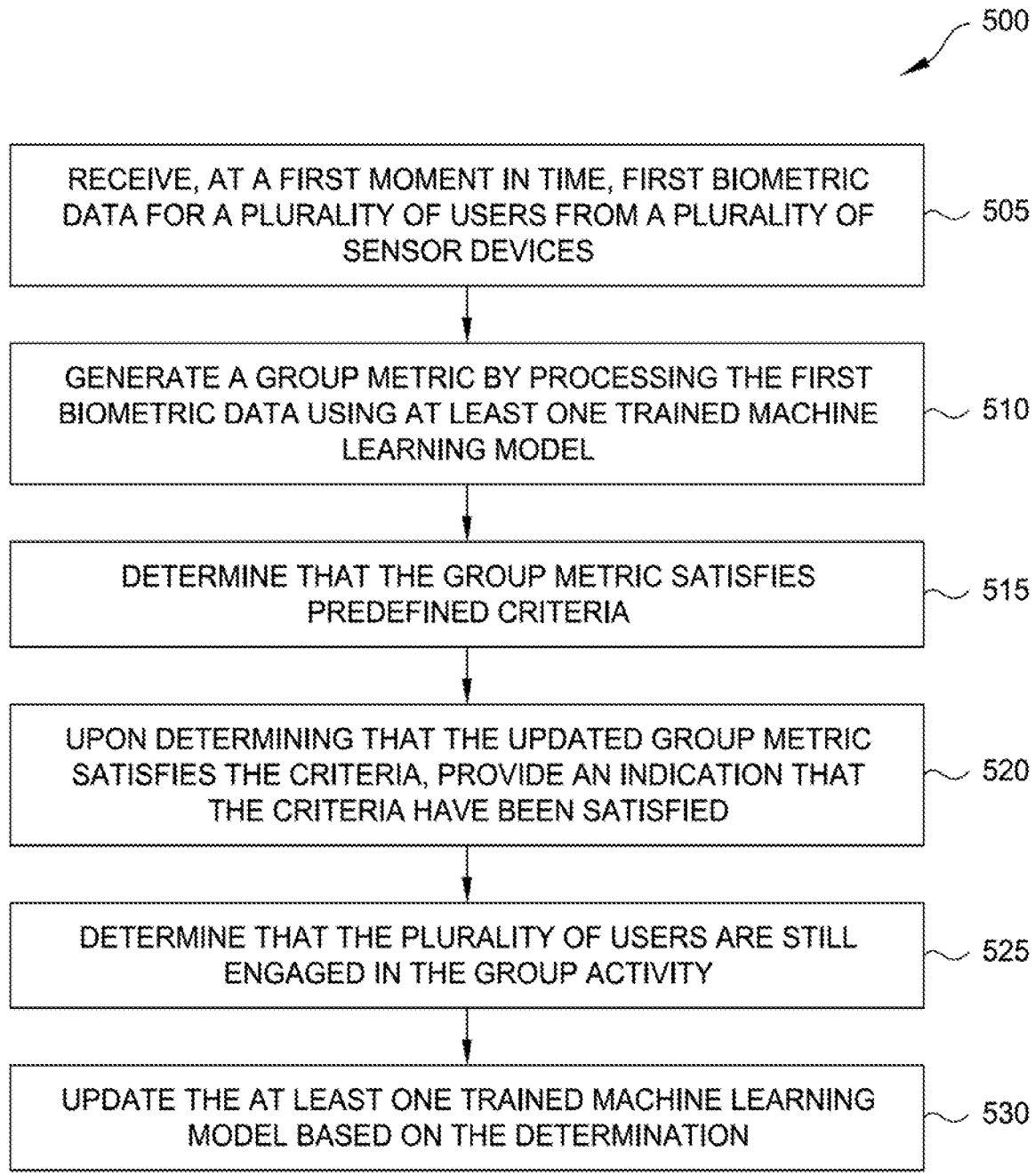
FIG. 5 is a flow diagram illustrating a method for using machine learning to monitor biometric data, according to one embodiment disclosed herein.

FIG. 5 is a flow diagram illustrating a method 500 for using machine learning to monitor biometric data, according to one embodiment disclosed herein. The method 500 begins at block 505, where, at a first moment in time, first biometric data for a plurality of users is received from a plurality of sensor devices. Next, at block 510, Machine Learning Component 240 generates a group metric by processing the first biometric data using at least one trained machine learning model. At block 515, it is determined that the group metric satisfies predefined criteria. At block 520, upon determining that the updated group metric satisfies the criteria, an indication that the criteria have been satisfied is provided, for example, to a user or speaker. At block 525, Decision Server 220 determines that the plurality of users are still engaged in the group activity. Finally, at block 530, Model Training Component 250 updates the at least one trained machine learning model based on the determination.

Figure 6:
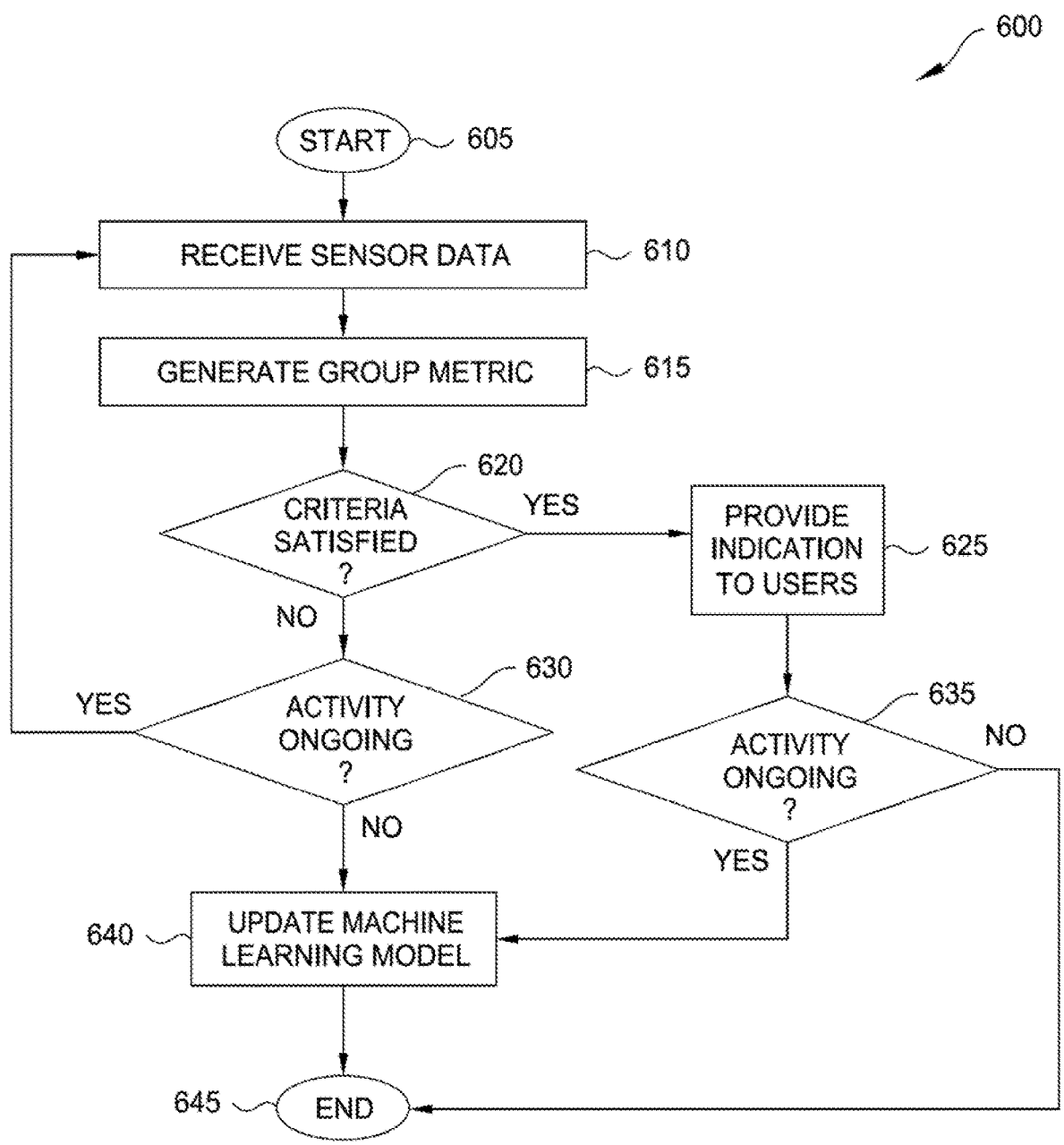
FIG. 6 is a flow diagram illustrating a method for using machine learning to monitor biometric data, according to one embodiment disclosed herein.

FIG. 6 is a flow diagram illustrating a method 600 for using machine learning to monitor biometric data, according to one embodiment disclosed herein. The method 600 begins at block 605, labeled START. At block 610, sensor data, e.g., biometric data collected from a user using a sensor device, is received. At block 615, the group metric is generated using machine learning models, such as Machine Learning Model 255. At block 620, it is determined whether the generated group metric satisfies the predefined criteria. If so, the method 600 proceeds to block 625, where an indication is provided that the criteria have been satisfied. For example, this indication could include a vibration or audio effect, or a message on a display. The method 600 then proceeds to block 635, where the system determines whether the group activity is still ongoing. In some embodiments, this determination may be made after a predefined period of time, for example, to give the users sufficient time to finish the current topic and begin their break. If the activity is still ongoing, the method 600 continues to block 640, where the Machine Learning Model 255 is updated in order to provide more accurate predictions in the future. For example, Model Training Component 250 can process the current biometric data from the users, as well as the determination that the users are not taking a break, to train and refine the respective Machine Learning Model 255. The method 600 then proceeds to block 645, where the method ends. If however, at block 635 it is determined that the activity is no longer ongoing, the method 600 proceeds to block 645, where the method ends.

Returning to block 620, if it is determined that the group metric does not satisfy predefined criteria, the method 600 continues to block 630, where the Decision Server 220 determines if the group's activity is still ongoing. If the activity has stopped, the method 600 proceeds to block 640, where the Machine Learning Model 255 is refined based on this determination, and then to block 645, where the method ends. For example, the most recent biometric data from the users is processed by Model Training Component 250, along with the determination that the users have interrupted the activity, to refine Machine Learning Models 255. If however, it is determined at block 630 that the activity is still ongoing, the method 600 returns to block 610, where sensor data is received from the users. In this way, the method 600 loops, analyzing data from the users, until the users either take a break or the criteria is satisfied.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the following, reference is made to embodiments presented in this disclosure. However, the scope of the present disclosure is not limited to specific described embodiments. Instead, any combination of the following features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the following aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

Aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Embodiments of the invention may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged only for the computing resources actually used (e.g. an amount of storage space consumed by a user or a number of virtualized systems instantiated by the user). A user can access any of the resources that reside in the cloud at any time, and from anywhere across the Internet. In context of the present invention, a user may access applications Machine Learning Component 240 or related data available in the cloud. For example, the Machine Learning Component 240 could execute on a computing system in the cloud. In such a case, the Machine Learning Component 240 could process biometric data of the users and store Machine Learning Models 255 at a storage location in the cloud. Doing so allows a user to access this information from any computing system attached to a network connected to the cloud (e.g., the Internet).

While the foregoing is directed to embodiments of the present invention, other and further embodiments of the invention may be devised without departing from the basic scope thereof, and the scope thereof is determined by the claims that follow.

What is claimed is:

1. A method, comprising:
  receiving, at a first moment in time, first biometric data for a plurality of users from a plurality of sensor devices;
  identifying, for each respective user of the plurality of users, a respective user category based on characteristics of the respective user;
  retrieving, for each respective user category, a respective trained machine learning model, wherein the respective trained machine learning model was trained specifically for users belonging to the respective user category;
  generating a group metric by processing the first biometric data using at least one trained machine learning model, wherein biometric data associated with each respective user is processed using the respective trained machine learning model corresponding to the respective user category identified based on characteristics of the respective user, comprising:
    processing a first subset of the first biometric data using a first trained machine learning model based on determining that each user associated with the first subset belongs to a first user category for which the first trained machine learning model was trained; and
    processing a second subset of the first biometric data using a second trained machine learning model based on determining that each user associated with the second subset belongs to a second user category for which the second trained machine learning model was trained;
  determining that the group metric does not satisfy one or more predefined criteria;
  receiving, at a second moment in time, second biometric data for the plurality of users from the plurality of sensor devices;
  generating an updated group metric by processing the second biometric data using the at least one trained machine learning model; and
  upon determining that the updated group metric satisfies the one or more predefined criteria, providing an indication that the one or more predefined criteria have been satisfied.

2. The method of claim 1, wherein the plurality of users are engaged in a group activity, and wherein the trained machine learning model is further refined using data from the plurality of users.

3. The method of claim 2, the method further comprising:
  upon providing the indication that the one or more predefined criteria have been satisfied, receiving, from at least one of the plurality of users, an indication that the at least one user wants to continue engaging in the group activity; and
  updating the at least one trained machine learning model based on the received indication.

4. The method of claim 2, the method further comprising:
  receiving, from at least one of the plurality of users, an indication that the at least one user wants to stop engaging in the group activity, wherein the indication is received prior to determining that the updated group metric satisfies the one or more predefined criteria; and
  updating the at least one trained machine learning model based on the received indication.

5. The method of claim 2, the method further comprising:
  determining, after providing the indication that the one or more predefined criteria have been satisfied, that the plurality of users are still engaged in the group activity; and
  updating the at least one trained machine learning model based on the determination.

6. The method of claim 2, the method further comprising:
  determining, before the one or more predefined criteria has been satisfied, that the plurality of users have stopped engaging in the group activity; and
  updating the at least one trained machine learning model based on the determination.

7. The method of claim 1, wherein generating the group metric comprises:
  aggregating the first biometric data from at least some of the plurality of users; and
  processing the aggregated biometric data using the at least one trained machine learning model.

8. The method of claim 1, wherein generating the group metric comprises:
  processing the biometric data for each respective user of the plurality of users using the at least one trained machine learning model to produce a plurality of individual metrics; and
  aggregating the individual metrics to form the group metric.

9. The method of claim 1, wherein the biometric data corresponding to at least one user is processed using a trained machine learning model that was trained using data from the at least one user.

10. The method of claim 1, wherein the biometric data includes at least one of:
  (i) a glucose level from each user;
  (ii) a lactate level from each user;
  (iii) a sodium level from each user;
  (iv) a potassium level from each user;
  (v) a heart rate from each user; and
  (vi) a temperature of each user.

11. A system, comprising:
  a processor; and
  a computer memory storing a program, which, when executed on the processor, performs an operation comprising:
    receiving, at a first moment in time, first biometric data for a plurality of users from a plurality of sensor devices;

identifying, for each respective user of the plurality of users, a respective user category based on characteristics of the respective user;

retrieving, for each respective user category, a respective trained machine learning model, wherein the respective trained machine learning model was trained specifically for users belonging to the respective user category;

generating a group metric by processing the first biometric data using at least one trained machine learning model, wherein biometric data associated with each respective user is processed using the respective trained machine learning model corresponding to the respective user category identified based on characteristics of the respective user, comprising:

processing a first subset of the first biometric data using a first trained machine learning model based on determining that each user associated with the first subset belongs to a first user category for which the first trained machine learning model was trained; and processing a second subset of the first biometric data using a second trained machine learning model based on determining that each user associated with the second subset belongs to a second user category for which the second trained machine learning model was trained;

determining that the group metric does not satisfy one or more predefined criteria;

receiving, at a second moment in time, second biometric data for the plurality of users from the plurality of sensor devices;

generating an updated group metric by processing the second biometric data using the at least one trained machine learning model; and upon determining that the updated group metric satisfies the one or more predefined criteria, providing an indication that the one or more predefined criteria have been satisfied.

12. The system of claim 11, wherein the plurality of users are engaged in a group activity, and wherein the trained machine learning model is further refined using data from the plurality of users, the operation further comprising:

determining, after providing the indication that the one or more predefined criteria have been satisfied, that the plurality of users are still engaged in the group activity; and updating the at least one trained machine learning model based on the determination.

13. The system of claim 11, wherein the plurality of users are engaged in a group activity, and wherein the trained machine learning model is further refined using data from the plurality of users, the operation further comprising:

determining, before the one or more predefined criteria have been satisfied, that the plurality of users have stopped engaging in the group activity; and updating the at least one trained machine learning model based on the determination.

14. The system of claim 11, wherein generating the group metric comprises:

aggregating the first biometric data from the plurality of users; and processing the aggregated biometric data using the at least one trained machine learning model.

15. The system of claim 11, wherein the biometric data corresponding to at least one user is processed using a trained machine learning model that was trained using data from the at least one user.

16. A computer-readable storage medium having computer-readable program code embodied therewith, the computer-readable program code executable by one or more computer processors to perform an operation comprising:

receiving, at a first moment in time, first biometric data for a plurality of users from a plurality of sensor devices;

identifying, for each respective user of the plurality of users, a respective user category based on characteristics of the respective user;

retrieving, for each respective user category, a respective trained machine learning model, wherein the respective trained machine learning model was trained specifically for users belonging to the respective user category;

generating a group metric by processing the first biometric data using at least one trained machine learning model, wherein biometric data associated with each respective user is processed using the respective trained machine learning model corresponding to the respective user category identified based on characteristics of the respective user, comprising:

processing a first subset of the first biometric data using a first trained machine learning model based on determining that each user associated with the first subset belongs to a first user category for which the first trained machine learning model was trained; and processing a second subset of the first biometric data using a second trained machine learning model based on determining that each user associated with the second subset belongs to a second user category for which the second trained machine learning model was trained;

determining that the group metric does not satisfy one or more predefined criteria;

receiving, at a second moment in time, second biometric data for the plurality of users from the plurality of sensor devices;

generating an updated group metric by processing the second biometric data using the at least one trained machine learning model; and upon determining that the updated group metric satisfies the one or more predefined criteria, providing an indication that the one or more predefined criteria have been satisfied.

17. The computer-readable storage medium of claim 16, wherein the plurality of users are engaged in a group activity, and wherein the trained machine learning model is further refined using data from the plurality of users, the operation further comprising:

determining, after providing the indication that the one or more predefined criteria have been satisfied, that the plurality of users are still engaged in the group activity; and updating the at least one trained machine learning model based on the determination.

18. The computer-readable storage medium of claim 16, wherein the plurality of users are engaged in a group activity, and wherein the trained machine learning model is further refined using data from the plurality of users, the operation further comprising:

determining, before the one or more predefined criteria have been satisfied, that the plurality of users have stopped engaging in the group activity; and updating the at least one trained machine learning model based on the determination.

19. The computer-readable storage medium of claim 16, wherein generating the group metric comprises:
   aggregating the first biometric data from the plurality of users; and
   processing the aggregated biometric data using the at least one trained machine learning model.

20. The computer-readable storage medium of claim 16, wherein the biometric data corresponding to at least one user is processed using a trained machine learning model that was trained using data from the at least one user.

* * * * *